United States Patent [19]

Bierman

[11] Patent Number: 5,508,030
[45] Date of Patent: Apr. 16, 1996

[54] CREATING NEW CAPILLARY BLOOD POOLS FOR PRACTICING BIDIRECTIONAL MEDICINE

[76] Inventor: Howard R. Bierman, 150 N. Robertson Blvd., Ste. 314, Beverly Hills, Calif. 90211

[21] Appl. No.: 102,448

[22] Filed: Aug. 5, 1993

[51] Int. Cl.$^6$ ..................................... A61K 45/05
[52] U.S. Cl. .................. 424/85.1; 424/85.2; 530/399; 514/12
[58] Field of Search ................... 424/85.1, 85.2; 514/12, 23, 503, 573, 738, 355; 530/399; 562/503; 568/852; 546/316

[56] References Cited

U.S. PATENT DOCUMENTS

| | | | |
|---|---|---|---|
| 4,994,559 | 2/1991 | Moscatelli et al. | 530/399 |
| 5,128,321 | 7/1992 | Murray et al. | 514/12 |
| 5,201,728 | 4/1993 | Giampapa | 604/890.1 |
| 5,213,568 | 5/1993 | Lattin et al. | 604/20 |
| 5,332,804 | 7/1994 | Horkiewicz et al. | 530/399 |

OTHER PUBLICATIONS

Lynch et al., PNAS, vol. 84, pp. 7696–7700, 1987.
Bedard et al., PNAS, vol. 84, pp. 6715–6719, 1987.
Deuel et al., Ann. Rev. Med., vol. 42, pp. 567–584 1991.
Linder et al., J Clin Invest., vol. 85, pp. 2004–2008, 1990.
West D. C. et al., Science, vol. 228, pp. 1324–1326, 1985.
Kahaleb, M. B., Rheumatic Disease Clinics of North America vol. 16(1) pp. 53–73, 1990.
Bevilacqua et al., J. Clin Invest, vol. 76, pp. 2003–2011, 1985.
Klagsburn et al., Ann. Rev. Physio., vol. 53, pp. 217–239, 1991.
Takahashi et al., Cancer Res., vol. 54, pp. 4233–4237, 1994.
Dobson et al., Cell, vol. 61, pp. 223–230, 1990.
Shen et al., Blood, vol. 81(10), pp. 2767–2773, 1993.
Folkman et al., Science, vol. 235, pp. 442–447, 1987.
Baird et al., "Peptide Growth Factors & Their Receptors I," Chapter 7, Eds. Sporn et al., Springer–Verlag, 1990.
Bolander, Proc. Soc. Exp. Biol. Med., vol. 200(2), pp. 165–170, 1992.
Folkman et al., Science, vol. 235, pp. 442–447, 1987.
Furcht et al., Lab. Invest., vol. 55(5) pp. 505–509, 1986.
Konrad, "Biological Barriers to Protein Delivery", Eds. Andus et al., Plenum Press, Chap. 14, 1993.

*Primary Examiner*—Chhaya D. Sayala
*Attorney, Agent, or Firm*—Albert M. Herzig

[57] ABSTRACT

A process is disclosed for stimulating capillary growth to form a capillary pool in a predetermined location of a mammal's body. This process creating a capillary pool may be used to introduce effective medications and other therapeutic agents unaltered in bio-availability through the skin which has been thinned to less than three millimeters thick. The capillary pool also permits detection of electrochemical signals from the circulating blood by sensors. These sensors can interpret chemical components of the blood such as oxygen, glucose, sodium, potassium and other elements and can be recorded from the sensor to devices that document chemicals in the blood continuously which is a much improved representation of what is happening physiologically without time restrictions. The capillary pool restores impaired blood circulation, facilitates removal of impurities from the blood, and can serve as a substitute blood supply for vascular-deficient body organs and tissues.

12 Claims, 2 Drawing Sheets

CREATING NEW CAPILLARY BLOOD POOLS FOR PRACTICING BIDIRECTIONAL MEDICINE

BACKGROUND OF THE INVENTION

The present invention relates to (A) the promotion of vascular growth of new capillaries in a spherical pool in a preselected area as close to the skin surface as possible within the human or animal body. The proximity of this newly formed spherical capillary pool (vascular pool) beneath the defatted thinned skin allows for bidirectional application of introduction of chemical agents (B). This allows for rapid and accurate transcutaneous absorption of any suitable medication (which term includes all drugs and other agents) into the circulation. The selection of appropriate highly charged chemical elements. For example, fluorides will accelerate the transcutaneous passage through the thinned skin directly into the circulation of the capillary pool without alteration or loss of bio-availability.

The capillary pool (C) may also be employed to detect electrochemical charges emitting from various blood elements circulating in the capillary pool to pass in reverse direction through the skin to an appropriate sensor overlying the capillary pool.

Broadly, three OBJECTS of this invention are:

A. Developing a new blood vessel capillary pool.

B. Transmitting chemical medications and other physical substances and elements directly into the bloodstream for controllable and predictable responses.

C. Transmitting immuno-biochemical information from the blood pool to sensors applied to the external surface of the skin thinned and defatted, as by acetone. The transmission of electrochemical signals from the blood elements in the circulation in reverse direction from the capillary pool through the thinned skin (opposite to conventional methods) to a sensor applied over the capillary pool. Biochemical and/or electrochemical sensors can be employed. The sensor therefore can directly read these signals from many chemical substances circulating in the blood. Thus, it is also possible to electrochemically detect oxygen, carbon dioxide, the pH of blood, and the percent saturation of oxygen.

Medications are administered orally, or injected directly into the vascular system, or absorbed into the vascular system transcutaneously. Introducing medications through oral administration is followed by absorption through the stomach and intestines. Some substances ingested orally are altered by the digestive system in or en route to the vascular system. Sometimes less than 50% of the substance is available in an effective form for absorption and treatment. Therefore, some substances are not suitable for oral administration, others are less effective when they reach the vascular system, thus decreasing the intended benefit at the target or organ for which the substance was intended.

The oral route for introducing medicines is often not preferred because of unfavorable side effects (for example, fluoride salts administered orally form hydrofluoric acid in the stomach, discomforting the patient). Needle puncture and other conventional entry techniques often do not provide continuous easy accessibility to the blood. Piercing the skin for long periods introduces the threat of bleeding, clotting and infection. Also, blood vessels may collapse or become blocked after extended use for introduction of medications.

Furthermore, the oral administration or subcutaneous injection require absorption time, during which the tissues and fluids can bind the medicine or alter its effectiveness.

Another current method for introducing medicine is by absorption through the skin. This method has limited application due to slow absorption rates in the skin surface. Also, tissue fluids bind or alter effectiveness before it is absorbed into the vascular system. Therefore, doses of a medicine otherwise administered must often be wastefully larger.

Accordingly, there has existed a definite need for a simple, efficient, safe, rapid and effective means of introducing substances into the vascular system and for avoiding problems associated with needle dislodgement.

Basic elements are known and employed in this new proposal:

In the prior art of transdermal passage of medications through the skin, the amount of absorption is relatively small and often uncontrollable.

Those transdermal medications react as they would by the intravenous route and are often highly variable. Yet, the chemical/medication reaction is unchanged. Many medications are partially insoluble and do not transmit well through the skin.

Conventional transdermal delivery is virtually useless for delivery of peptide drugs whose sizes are too big and too fat-insoluble to pass-through the fat layers of the skin and the underlying subcutaneous blood vessels.

Fortunately, now there exist many available (in their rapidly growing field) sensors that can function when introduced into the venous or arterial circulation. The newly developed capillary blood pool of this invention does not use an implanted indwelling blood sensor. The sensor is applied to the thinned skin surface over the capillary pool. Therein the sensors can transmit or receive information continuously for blood glucose or tissue fluid glucose concentration for controlling and/or treating, and transmit that data to an external receiver. These sensor devices are now available for a use with this invention to measure glucose, urea, antibiotics, and many other relevant chemical substances to transmit and receive, and interpret, and treat medical conditions with this information obtained from this capillary pool for individual patients (see 1. Velho, Froguel, Sternberg, Thevenot, Reach, "In vitro and In vivo Stability of Electrode Potentials In Needle-Type Glucose Sensors", Diabetes, vol. 38: 164–171, 1989.

2. Bard, Faulkner, "Electrochemical methods", Fundamentals and Applications. New York, Wiley, 1980.

3. Hitchman, "Measurement of Dissolved Oxygen", Geneva, Wiley/Orbisphere, 1978

4. Ives, Janz, "General and Theoretical Introduction!', Reference Electrodes, Theory and Practice, New York Academic, 1961.

5. Armour, Lucisano, McKean, Gough, "Application of Chronic intravascular Blood Glucose Sensor in Dogs", Diabetes, vol 39: 1519–1526, 1990.

6. McKean, Gough, "A Telemetry-Instrumentation System for Chronically Implanted Glucose and Oxygen Sensors", IEEE Trans Biomed Eng 35: 52 6–32, 1988).

Another object of the invention is to improve and accelerate the absorption of substances and medications through the skin in minimal volume for short or long periods with much better control and predictability. Conventional transcutaneous absorption is relatively small and wherein the chemical reactions from the medication react as they would by the intravenous route but in much less degree, again, often uncontrollable. The major object and result of the capillary pool is that the chemical/medication reaction is unchanged so that the passage through the thinned skin does not alter the chemical reaction.

Transmitting accurate amounts of chemical elements and medications, and biological substances through the skin directly into the capillary blood circulation, and thence into the entire circulation almost immediately, the control of the amount of agents that are being transcutaneously introduced into the circulation, makes it possible to introduce oxygen, and other readily exchangeable gases, and chemical and physical agents, including antibiotics. Other therapeutic substances would permit the acceleration of absorption of substances to readily accessible circulation in minimal volume for short or long term periods, with small amounts of medication and with much higher control and more predictable results for long-term, continuous use.

This could also afford ready access if necessary to obtain blood samples from an easily accessible capillary pool for chemical determinations or other means for administering materials which may be life saving. This would avoid searching for conventional blood vessels particularly when patients may be in shock and have no discernible blood pressure. The capillary pool will always remain available. This would be much more effective than subcutaneous or intramuscular injections.

An equally important feature is to allow information to be obtained continuously from the capillary pool through the capillary wall and skin to an external sensor in close proximity positioned over the capillary pool. These sensors are functional by electrochemical transmission, but it has up to this time required direct insertion of a sensitive electrode into the bloodstream by needle or catheter implantation. This invention now permits the newly vascularized capillary pool to transmit that information directly through the skin onto a cutaneous sensor without implantation by conventional methods. This will allow the bloodstream to read directly onto an overlying sensor which can determine blood sugar for use in diabetes control; for sodium and potassium and other chemical elements which are often critically needed in the daily medical control of many patients. For example, the sensor signal of excess blood sugar can trigger the release of insulin through another capillary pool to control the blood sugar level. In reality it could serve as an electronic pancreas blood sugar regulation in diabetes. This signal can also be received telemetrically at a central receiving station in a hospital or medical building or even physician's offices which permit daily home care, or for alerting patients at their daily occupation. This opens a great opportunity for determining medical care of patients on a continuous basis while performing daily tasks or even at sleep or at rest.

SUMMARY OF THE INVENTION

The present invention discloses a method of stimulating capillary vascular growth to form a spherical capillary pool in a predetermined location close to and via an extremely thinned skin surface, to provide a potential for receiving, transmitting and controlling medicinal treatment via usable technology and direct intravascular administration of medicines via transcutaneous passage as disclosed.

By producing a new highly vascular capillary pool situated just beneath a thinned layer of skin less than 3 mm thick, allows a metered amount of unaltered drug to pass-through this very thinned skin which is depleted of fat. Furthermore, by using highly charged, hydrostatic chemical drugs, peptides and elemental substances, e.g., fluorides, the electrochemical charges of these hydrostatic materials will force these substances through the skin via the hair follicles and sweat glands into the newly developed vascular capillary pool in humans, horses, dogs, rodents and other animals.

Through knowledge of hydrostatics and osmosis and semipermeability of membranes, passage of solvents into a relevant area can be controlled within the skill of medical arts and science. This includes influencing the passage of positive gradient flow and usable intelligence to and/or from the capillary pool and selectively in and/or out of the body's circulatory system.

A capillary wall is a semipermeable membrane one cell layer thick. Fluid or a suspension of material outside of the capillary pool exerts a hydrostatic pressure. At the same time, blood circulating within the capillary exerts an osmotic pressure.

When the osmotic pressure within the capillary circulation is equal to the hydrostatic pressure outside of the capillary wall, there is no passage of chemicals through the capillary wall, in either direction. However, when the substances of increased hydrostatic pressure outside of the capillary pool have greater than the osmotic pressure within the circulation, movement into the circulation is favored. As long as that hydrostatic pressure material is maintained, there will be a positive gradient of flow from outside the capillary pool into the circulation.

Thus, a suspension outside of the capillary pool of potassium flouride, or other substances which contain an increased hydrostatic pressure, the gradient will drive the chemical elements and substances through the thinned skin and semipermeable capillary wall into the circulation. Furthermore, instantaneous control can be exerted by reducing the hydrostatic pressure of the chemical substance by inactivation or dilution, therefore, shutting off the positive gradient from outside the capillary pool into the circulation.

This invention includes the steps of (a) selecting an area in which a "blood pool", i.e., a dense concentration of capillaries, is conveniently located, (b) first injecting several solutions of isotonic saline into this area to form a well in the skin tissue, and (c) then injecting a second solution, comprising at least one angiogenic vascular stimulant, into the well. The angiogenic agent provokes blood vessel formation and the resulting capillary "pool" (vascular sphere) provides an area of increased blood concentration and an additional vascular pathway through which easily accessible blood is readily available close to the surface of the skin.

The area which is selected may be located anywhere desired. The location is dependent on the primary purpose for which the capillary pool is being generated. For example, if the pool is to augment blood flow in an area having partially or totally blocked blood vessels, the location will be selected for its proximity to the area requiring supplemental blood flow. If the pool is to provide increased effectiveness in the transcutaneous to intravascular administration of medications and other therapeutic agents, the pool will preferably be located near the skin surface within the easy reach of the patient, readily accessible, and visible. Both purposes can be combined.

Therapeutic levels of medications, mixed with carriers which enhance skin permeability, are then placed over the vascular sphere located beneath the skin surface and through which it enters the bloodstream. The medication is thus transported through the very thinned layer of skin directly into the vascular system without need for a needle and without the delays and side effects of oral or venous administration. Medications may also be injected directly into the vascular sphere for immediate action, or blood can be easily removed therefrom.

The capillary pool contains electrochemical signals from the various substances in the circulating blood. These electrochemical signals can be detected as they penetrate the capillary walls through the overlying thinned skin by an appropriate sensor, known to the art, applied to the external surface of the skin. The capillary pool does not require an implanted invasive intravascular electrode or similar device.

Other features and advantages of the present invention should become apparent from the following description of the preferred process, taken in conjunction with the accompanying drawings, which illustrate by way of example the principles of the invention.

The schematic illustrations (FIGS. 5, 6 and 7) demonstrate the importance of the thinned skin that permits exceptional transfer bidirectionally from the patch to the pool and electrochemical signals from the pool to the sensor. The development of the capillary pool from its inception is placed just beneath the dermal layer of the skin, and subsequent injections of the angiogenic stimulants in this close proximity to the skin thereby make the covering layer of the skin within or less than 3 mm as compared to the normal skin of 5 mm or greater.

DETAILED DESCRIPTION OF THE PREFERRED EMBODIMENT

Vascular aggregations formed in accordance with the process of the present invention are capillary pools located in a preselected area of the body, and are generally 2 to 7 cm in diameter. This vascular sphere may be located near the skin surface or it may be located in or near a body organ at a location lacking in blood flow due to failed or impaired circulation such as that caused by a stroke or by blockage of a blood vessel. For capillary pools located near the skin surface, preferably the location is permanently marked such as with a tattoo to allow for accuracy in locating the pool when administering medication and other therapeutic substances.

In an initial step, the desired location of a capillary pool is selected. The location will be within the subcutaneous tissue near the skin surface, preferably in a body location easily reached by the person administering the medication or other therapeutic agents. An example of a preferred location on a human body is on the front of the torso at about abdomen level allowing for self administration of substances if desired.

FIGS. 1 through 4 of the drawings illustrate the formation and the method of formation of the capillary pool.

Figure 5:
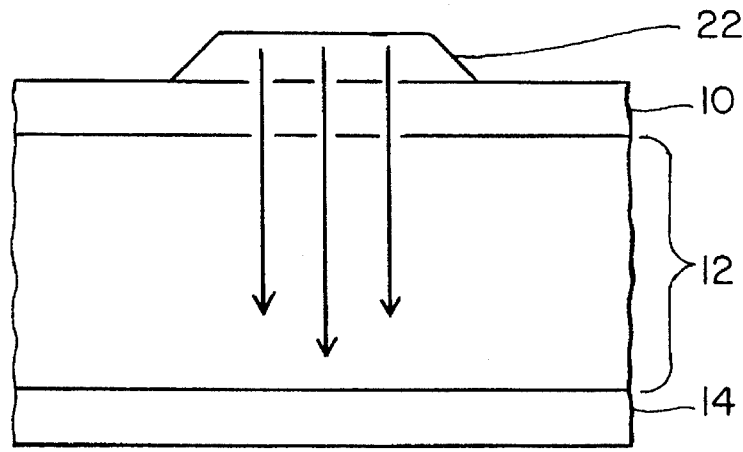
FIG. 5 is a schematic depiction of application of medication through a conventional patch—showing substances passing through normal skin (5 mm) thickness to scattered blood vessels in the subcutaneous tissue, without a capillary pool.

FIG. 5 is a schematic drawing illustrating a conventional patch with substances passing through normal skin (5 mm) thickness to scattered blood vessels in the subcutaneous tissue.

Figure 6:
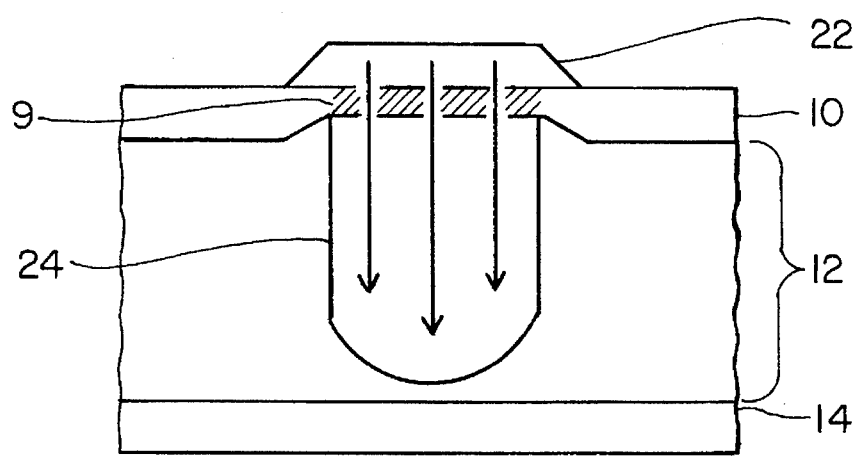
FIG. 6 is a schematic depiction of the transcutaneous passage of patch substances through a thinned layer of skin, less than 3 mm in thickness to a highly vascularized new capillary pool developed by this invention allowing much greater penetration and rapid entry into the circulation.
Figure 7:
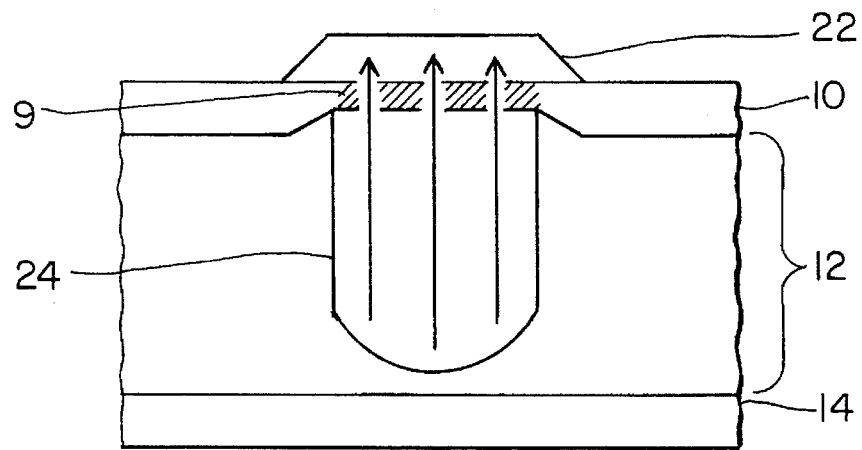
FIG. 7 is a schematic depiction of the transcutaneous passage of electrochemical radiation from the circulating blood in the highly vascularized capillary pool through the thinned skin 9 to reach the electronic receptors in the sensors, which then can be transmitted to display into—or trigger devices subautomatically or manually to remedy abnormalities through a patch. The capillary pool may be divided into both ingress and egress. Ingress is indicated by descending vertical arrows in FIG. 6, and egress is shown by ascending vertical arrows in FIG. 7.

FIGS. 6 and 7 are schematic illustrations of the skin and capillary pool as employed in the practice of this invention.

A cross-section of skin (FIG. 1) is composed of the epidermis (outer layer) 10, and the dermis (inner layer) 11, the germinating cells of the skin. Below the skin is the subcutaneous tissue 12. The fascia 14 separates the subcutaneous tissue 12 from the muscle tissue 15. The subcutaneous tissue 12 contains fat cells, blood vessels 13, lymph vessels, and polysaccharides (hyaluronic acid, glycosaminoglycans).

Figure 1:
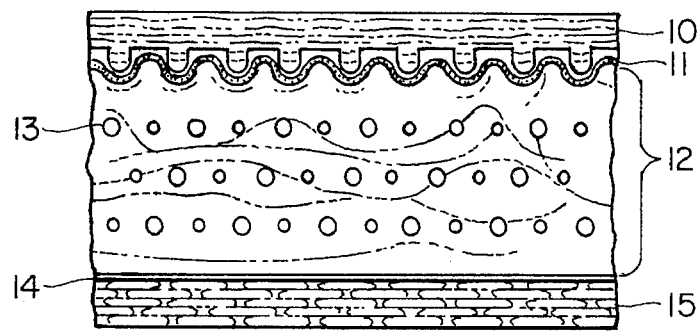
FIG. 1 is a simplified depiction of a cross-section of skin and underlying body tissue.
Figure 2:
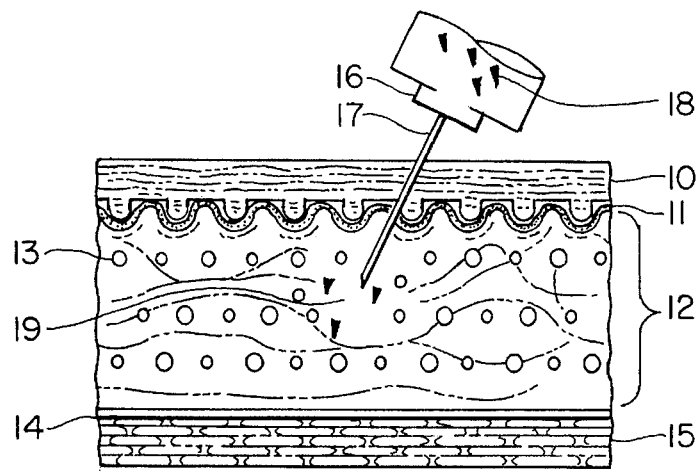
FIG. 2 is a simplified depiction of a cross-section of skin and underlying body tissue undergoing injection of the saline first solution in accordance with the process of the present invention.

FIG. 2 shows a first solution 18 is injected into the subcutaneous tissue 12 using a needle 17 and syringe 16. The first solution thus creates a well 19 (reservoir) by separating the tissues. The first solution used in the method may be any inert solution. Preferably, the first solution is an isotonic saline solution 18 having a salinity level resembling the natural saline concentration in bodily fluids. Preferably, between about 3 and 6 cc's of the first solution are injected promptly depending on the size of the well desired as well as on the nature of the tissue which is being injected. Specifically, skin tissue can adapt to higher level initial injections without adverse side effects. This preparatory saline injection may be repeated in the same spot three or more times promptly within two hours, and creates a bubble of saline.

Figure 3:
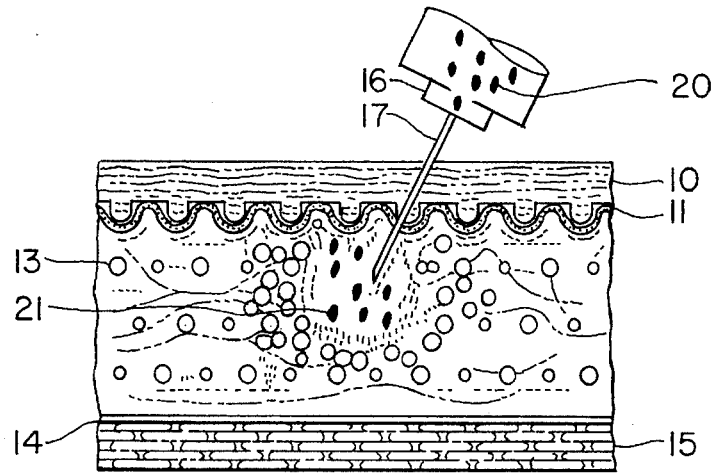
FIG. 3 is a simplified depiction of a cross-section of skin and underlying body tissue undergoing injection of the second solution in accordance with the process of the present invention.

After a period of time, generally between about 4 hours and 24 hours, a second solution 20 is injected into the well 19 formed by the saline solution (FIG. 3). The second solution contains at least one angiogenic stimulant which promotes vascular growth. Preferably, between about 3 and 10 cc's of the second solution are injected. Thus, the capillaries 13 are stimulated and in conjunction with the proliferative polysaccharides in the subcutaneous tissues form new capillaries within the well 19. A controlled active microvessel proliferation is produced by administration of angiogenic stimulants and a capillary pool 24 is thereby formed within about 7 to 21 days. Preferably, a permanent marking 23 is placed on the skin such as a tattoo or indelible marker above the capillary pool location for accurate determination of the site on which to place medications for the most effective action.

The angiogenic stimulants have at least one proliferating element that affects the endothelial cells to initiate formation of capillaries (tiny blood vessels having walls about one cell layer thick). There are many angiogenic stimulants that each react somewhat differently and have different properties and side effects. Thus, the optimum second solution may contain either one or a mixture of two or more angiogenic stimulants and the selection will depend upon the application desired. The angiogenic stimulant may be selected from highly differentiated compounds such as 1-butyryl glycerol (monobutyrin); polypeptides; alpha and beta transforming growth factors; angiogenic substances such as interleukin 1, interleukin 4, and other angiogenic factors; tumor necrosis factor; platelet derived growth factor (PDGF); fibroblastic growth factors (FGF's); and non-peptide angiogenic agents such as prostaglandins (PGE1 & PGE2), hyaluronic acid fragments and nicotinamide related compounds. One combination of angiogenic stimulants that has proven effective for stimulating capillary formation is interleukin 4, endothelin, fibroblastic growth factor. These elements in combination provide rapid and effective formation of capillary pools within the subcutaneous tissue. The B chain homodimer of platelet derived growth factor is one of the more effective individual angiogenic stimulants having high mitogenic and neovascular activity.

Figure 4:
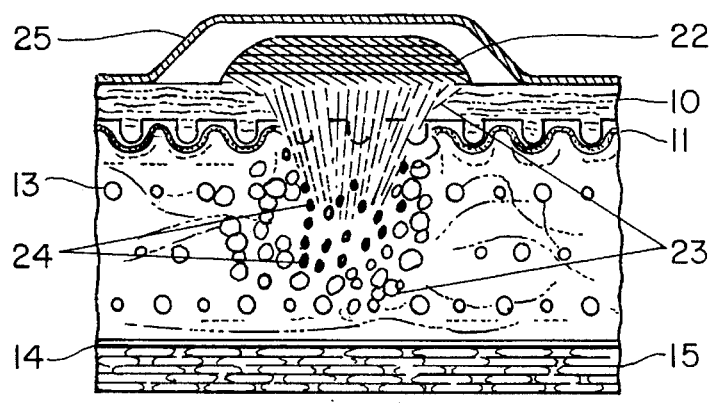
FIG. 4 is a simplified depiction of a cross-section of skin and underlying body tissue after formation of the capillary pool in accordance with the process of the present invention and a depiction of medication in place for transcutaneous use.

FIGS. 4, 6 and 7 demonstrate that the capillary pool 24, once formed, may be used for transcutaneous absorption of medications and other therapeutic agents. Use of the capillary pool produced by the process of the present invention is especially desirable in patients requiring frequent dosages of medications for long-term problems such as diabetes, cancer, and heart disease. For example, fluorides in frequent dosages are useful in treatment of a variety of bone diseases, as well as in prevention of osteoporosis and tooth decay. Fluoride salts mixed with carriers that increase skin permeability are placed on the skin over the capillary pool 24 in a transcutaneous patch 22 and covered with adhesive tape (sterile dressing) 25 for absorption into the vascular system. The capillary pool is also useful in cases of shock where blood vessels have collapsed, provided (due to time constraints) that the capillary pool has been formed prior to the patient going into shock.

Due to the proximity of many capillaries to the skin, the surface of the skin above the capillary pool is warmed. Warmth aids in increasing the transcutaneous absorption of medication, thus, the rate of absorption through the skin into the capillary pool is increased. Absorptivity is further enhanced by dissolving or suspending the medication or other therapeutic agent in a carrier that increases skin permeability. Examples of commonly used carriers suitable for the present purposes are isopropyl myristate, propylene glycols, dimethyl-sulfoxide, and combinations and mixtures thereof. The carriers affect the rate of absorption, as does the medication's solubility in the particular carrier. Thus, dosage of medication can be controlled through the selective use of carriers.

It will be seen that a major object of the invention is to create a new blood vessel system for bidirectional medicinal use. This system consists of multiple capillaries bunched together in at least one specific localized area of 2 to 7 cm in diameter that is readily accessible to the subject, for example, just beneath the skin of the abdomen or lower extremities. The capillaries lie immediately beneath the surface of the epidermis or outer layer 10. The capillary depth beneath said upper surface should be no more than 3 millimeters. The capillary pool does not require an implanted invasive intravascular electrode or similar device. The capillary pool contains electrochemical signals from the various substances in the circulating blood. These electrochemical signals can be detected as they penetrate the capillary walls through the overlying thinned skin by an appropriate sensor, known to the art, applied to the external surface of the skin.

Additional information on the transcutaneous capillary pool is that once the sensor has detected abnormality as in the sugar level of a diabetic, this sensor signal can in turn be connected to an insulin dispenser which can then administer insulin via the same or another capillary pool so that an elevated blood sugar can then be corrected immediately with measured amounts of insulin administered transcutaneously via such capillary pool administration of insulin directly into the bloodstream. Therefore, much smaller amounts of insulin will be required to be dispensed transcutaneously, for maintaining control of the diabetes. In other words an artificial pancreas for long term insulin administration on appropriate demand from the blood sugar concentration.

Dispenser with the capillary pool therefore operates where the sugar concentration determines whether insulin is to be administered in smaller or larger amounts. If the blood sugar level is too low, the sensor signal could alert the patient to take sugar. In other words, acting very much as a substitute for the beta cell which is the glucose sensitive cell in the pancreas, without having to have any implantation of an electrode sensor. This is all done extracutaneously as read from the capillary pool, blood sugar from the capillary pool to the skin surface, and the external sensor, reading the blood sugar level. This can also be similarly approached in treatments of other conditions such as cortisone deficiencies, as in Addison's disease, in cardiac conditions, requiring vascular dilation of the coronary arteries, and other arteries, particularly in strokes, and where continuous administration of very critical medication may be life saving and protection against arrhythmias and other cardiac abnormalities.

A new blood vessel circulation is thus created for supplying an area that is starved from nutrition and oxygen, and removal of carbon dioxide and other elements because of the lack of blood supply directly into that area, and to restore the circulation that has been impaired. This can be applied to the heart, in the brain in case of strokes, into the nervous system (spinal cord and smaller nerves), and areas which have been deprived of circulation by virtue of injuries, and replacing circulation in various organs such as the liver in cirrhosis, diseases of the kidney, the lungs in emphysema, and other organs.

Although the invention has been described in detail with reference only to a preferred embodiment and process, those of ordinary skill in the art will appreciate that various modifications can be made without departing from the spirit of the invention. Accordingly, the invention is defined by the following claims:

I claim:

1. A method of creating a capillary blood pool in subcutaneous tissue below the skin of a mammal, comprising the steps of:

a) selecting an area of the skin of the mammal below which a capillary blood pool is to be developed within subcutaneous tissue of said mammal;

b) injecting a first solution of isotonic saline into the subcutaneous tissue below the selected area of skin of said mammal to form a well area of said solution in said tissue; and c) injecting a second solution comprised of at least one angiogenic stimulant selected from the group of compounds consisting of 1-butyryl glycerol, alpha transforming growth factor, beta transforming growth factor, interleukin 1, interleukin 4, tumor necrosis factor, platelet derived growth factor, prostaglandin, hyaluronic acid fragments, nicotinamide and fibroblastic growth factor, into said well area thereby stimulating new capillary growth within said well area and forming a capillary blood pool therein.

2. The method of claim 1 wherein the skin of said mammal in the selected area of the skin is thinned to within 3 millimeters of the subcutaneous tissue below said selected area by the injection of saline.

3. The method of claim 1 wherein the location of the capillary blood pool is indicated by marking the skin of said mammal at the selected area.

4. The method of claim 1 wherein the time interval between the injection of said first solution and the injection of said second solution is between 2 and 24 hours.

5. A method of creating a capillary blood pool created in subcutaneous tissue below the skin of a human patient, comprising the steps of:
   a) selecting an area of the skin of said patient readily accessible and visible to said patient and to a physician below which a capillary blood pool is to be developed within subcutaneous tissue of said patient;
   b) injecting a first solution of isotonic saline into the subcutaneous tissue below the selected area of skin of said patient to form a well area of said solution in said tissue; and
   c) injecting a second solution comprised of at least one angiogenic stimulant selected from the group of compounds consisting of 1-butyryl glycerol, alpha transforming growth factor, beta transforming growth factor, interleukin 1, interleukin 4, tumor necrosis factor, platelet derived growth factor, prostaglandin, hyaluronic acid fragments, nicotinamide and fibroblastic growth factor, into said well area thereby stimulating new capillary growth within said well area and forming a capillary blood pool therein.

6. The method of claim 1 wherein the selected area of the skin of said human subject below which said capillary blood pool is formed in a body location easily reached by said subject or other person administrating therapeutic medications via introduction into said blood pool.

7. The method of claim 1 wherein the first solution of isotonic saline in an amount of between about 3 cc and about 6 cc is injected less than 3 mm into subcutaneous tissue below the selected area of skin of said subject thus creating said well area and promoting the separation of fat tissues.

8. The method of claim 7 wherein the first solution of isotonic saline is injected into said subcutaneous tissue three or more times within a two hour period thereby creating a bubble of saline in said well area.

9. The method of claim 1 wherein the second solution, comprised of at least one angiogenic stimulant in a solution amount of between about 3 cc and about 10 cc, is injected into said well area from about 4 hours to about 24 hours after the creation of said well area by said first solution whereby said capillary blood pool is formed within about 7 days to about 21 days.

10. The method of claim 1 wherein the angiogenic stimulant or stimulants of said second solution stimulate endothelial cells within said well area to initiate formation of blood capillaries to form said blood pool.

11. The method of claim 1 wherein interleukin 4, endothelin and fiberblastic growth factor are angiogenic stimulants combined to form said second solution and promote rapid and effective formation of said capillary blood pool.

12. The method of claim 1 wherein B chain homodimer of platelet derived growth factor as an angiogenic stimulant having high mitogenic and neovascular activity forms said second solution.

\* \* \* \* \*